United States Patent [19]
Totakura

[11] Patent Number: 5,954,748
[45] Date of Patent: Sep. 21, 1999

[54] GELATIN COATED GUT SUTURE

[75] Inventor: Nagabhushanam Totakura, North Haven, Conn.

[73] Assignee: United States Surgical Corporation, Norwalk, Conn.

[21] Appl. No.: 08/680,387

[22] Filed: Jul. 15, 1996

[51] Int. Cl.[6] .................................................. A61B 17/04
[52] U.S. Cl. ........................ 606/229; 606/228; 606/230; 206/339; 427/2.1; 427/2.29
[58] Field of Search .................... 606/228–237; 206/339; 427/2.11, 2.22, 2.29

[56] References Cited

U.S. PATENT DOCUMENTS

| | | |
|---|---|---|
| 887,130 | 5/1908 | Schmidt . |
| 1,254,031 | 1/1918 | Davis . |
| 1,865,214 | 6/1932 | Saladino et al. . |
| 1,999,641 | 4/1935 | Sharp et al. . |
| 2,039,262 | 4/1936 | Schulte . |
| 2,457,804 | 1/1949 | Bower . |
| 2,475,697 | 7/1949 | Cresswell . |
| 2,484,813 | 10/1949 | Bower . |
| 2,493,943 | 1/1950 | Bower . |
| 2,524,772 | 10/1950 | Davis et al. . |
| 2,576,576 | 11/1951 | Cresswell et al. . |
| 2,637,321 | 5/1953 | Cresswell . |
| 2,640,752 | 6/1953 | Davis et al. . |
| 3,034,852 | 5/1962 | Nishihara . |
| 3,166,073 | 1/1965 | Kronenthal . |
| 3,276,448 | 10/1966 | Kronenthal ............................. 128/334 |
| 3,284,557 | 11/1966 | Polansky ................................. 264/238 |
| 3,698,853 | 10/1972 | Wilson . |
| 3,729,007 | 4/1973 | Mirkovich . |
| 3,808,113 | 4/1974 | Okamura ............................ 204/159.12 |
| 4,027,676 | 6/1977 | Mattei . |
| 4,201,216 | 5/1980 | Mattei . |
| 4,343,617 | 8/1982 | Baur, Jr. . |
| 4,433,688 | 2/1984 | Bichon . |
| 4,506,672 | 3/1985 | Bichon . |
| 5,089,013 | 2/1992 | Bezwada et al. . |
| 5,304,205 | 4/1994 | Shinoda et al. . |
| 5,342,624 | 8/1994 | McNeil et al. . |
| 5,442,032 | 8/1995 | Arnold et al. . |

*Primary Examiner*—Gary Jackson

[57] ABSTRACT

A catgut suture includes a cross linked gelatin coating which is substantially insoluble in tubing or storage solution. The gelatin coating is formed by immersing the gut suture in aqueous gelatin solution, fixing the gelatin in a solution of cross linking agent such as glutaraldehyde, buffering the coating, then drying the suture at a temperature of at least about 50° C.

20 Claims, 1 Drawing Sheet

GELATIN COATED GUT SUTURE

BACKGROUND

1. Technical Field

The subject matter disclosed and described herein relates to a surgical suture fabricated from gut and coated with gelatin, and a method for making same.

2. Background of the Art

Sutures are often used in surgical procedures for holding cut tissue surfaces in apposition for a period of time sufficient for healing. Non-absorbable sutures, e.g. sutures made from non-bioabsorbable materials such as polyolefins, nylon, cotton, and the like, are generally removed after a period of time. Absorbable sutures, e.g. those fabricated from bioabsorbable materials such as polymers of lactide and glycolide, collagen, and the like, are gradually degraded and absorbed by the body, and do not require subsequent removal.

Gut sutures are made from the submucosa layer of the intestines of animals (e.g., sheep, beef, etc.) which consist mainly of collagen. In preparing gut sutures and ligatures, animal intestinal tubes are split longitudinally, cleaned and spun or twisted to form strands. Such strands are termed plain catgut and when implanted in animal tissues are normally absorbed within a period of several days by enzymolysis. For many surgical procedures it is necessary for the sutures to retain their strength for a longer period of time to permit a wound or incision to heal properly. Therefore, such sutures are tanned by immersion in a solution of tanning agent such as a chromium salt. Tanning increases the resistance of collagenous material to hydrolytic attack. Such sutures are termed "chromic catgut".

Surgeons need sutures which are pliable and instantly usable. Unless catgut sutures are stored in a tubing solution, from which they are removed by the surgeon just prior to use, they will dry out and become too hard for use. Such storage solutions are well known in the art and typically include water and alcohol, for example, ethanol and/or isopropanol, and optionally triethanolamine.

SUMMARY

A method is provided herein for treating a gut suture to achieve superior handling characteristics. The suture is treated by contacting the gut suture with an aqueous solution of the gelatin to coat the suture with gelatin and then contacting the coated gut suture with at least one fixative agent to cross link the gelatin. In particularly useful embodiments the method further includes the steps of contacting the coated gut suture with buffer solution, and heating the coated suture to a temperature of at least about 50° C. for a predetermined period of time. The resulting coated gut suture can then be stored in tubing solution without losing the gelatin coating. Advantageously, even after being stored in tubing fluid the suture retains superior knot run down and fray resistance.

Optionally a plasticizer such as glycerol can be incorporated into the gelatin solution. Fixative agents can include for example, glutaraldehyde and/or formaldehyde.

The heating steps is optimally conducted in a vacuum or in a stream of flowing dry nitrogen for from abut 1 to about 20 hours.

BRIEF DESCRIPTION OF THE DRAWINGS

Various embodiments are described herein with reference to the drawings, wherein.

DETAILED DESCRIPTION OF PREFERRED EMBODIMENTS

Figure 1:
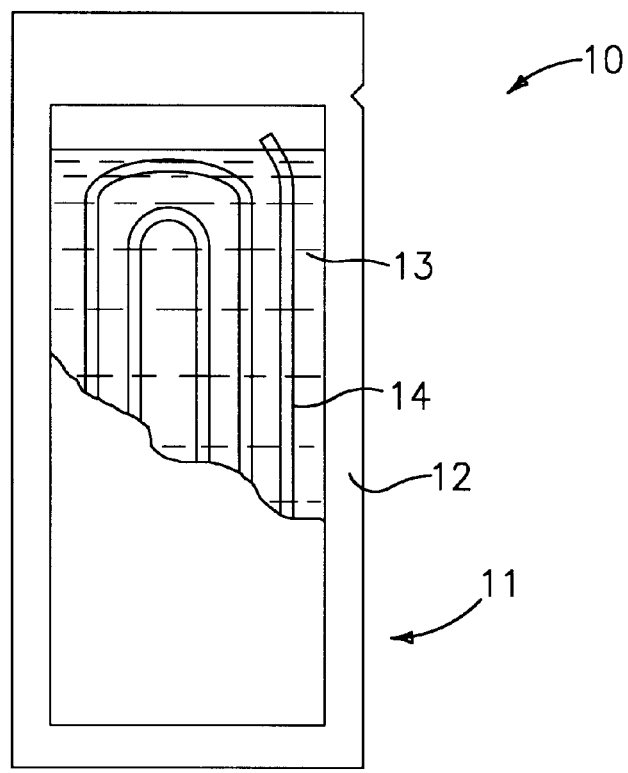
FIGS. 1 and 2 are cut-away views illustrating alternative embodiments of a suture package containing tubing fluid and a gut suture treated in accordance with the method described herein.
Figure 2:
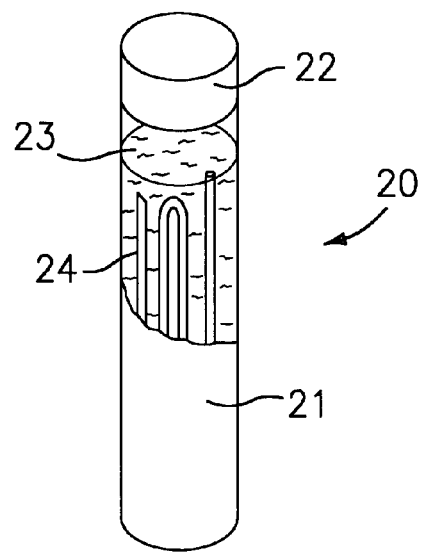

The pre-coated catgut sutures used in the method described below may be provided by conventional techniques. By way of illustration, beef serosa ribbons are desalinated and assembled. They are then soaked in wet phase treatment in baths of sodium carbonate, hydrogen peroxide, and water. Plain catguts are then soaked in sodium hydrosulfite and then soft water, whereas chromic catguts are then soaked in pyrogallic acid, sodium bichromate to which sodium bisulfite is later added, and optionally gelatin. After the wet phase treatments the wet catguts are then twisted. This operation blends the serosa lengths before the drying operation which creates chemical liaisons between the collagen molecules. After twisting the catguts are dried and cut to final length. The catguts are then machine polished. Chromic catguts are further soaked in an aqueous solution of ethanol and glycerine.

The above described process provides catgut sutures which may then be coated in accordance with the method described below. The coating method described herein advantageously provides a gelatin coating which surprisingly does not come off the suture even when the suture is stored in tubing solution. Thus, an important distinguishing feature of the present method is that the gelatin coating remains on the suture when the surgeon removes the suture from the tubing solution and provides improved knot run down and reduced fraying characteristics on an immediately usable suture.

The preferred method described herein comprises five basic steps which will be discussed in greater detail below: (1) soaking the suture in the coating agent solution, (2) soaking the suture in a fixative solution, (3) soaking the suture in a buffer, (4) drying the suture, and optionally (5) storing the suture in a tubing fluid.

The coating agent solution comprises an aqueous solution of gelatin in pyrogen free water. The gelatin is commercially available under the designation Vysegelatin, NF grade (225 Bloom, Type B, Calfskin, Supplied by Vysegelatin Company, Schiller Park, Ill. 60176. The solution preferably ranges in concentration of from about 1% to about 10% gelatin, more preferably from about 2% to about 8%, and most preferably from about 4% to about 6%. Percentages given herein are by weight unless otherwise specified. Optionally, a plasticizer, such as triethylcitrate, and/or glycerine or other polyhydric alcohols, can be included in the coating solution and preferably ranges up to about 6% of the coating solution composition, more preferably from about 0.05% to about 4%, and most preferably from about 0.5% to about 2% of the composition. The ratio of plasticizer amount to that of gelatin preferably ranges from about 0.0% to about 100%. The gelatin coating provides beneficial surface properties to the catgut suture by improving surface smoothness and reducing fraying. The plasticizer enhances the benefits of the gelatin coating.

The coating solution is optimally maintained at a temperature of at least 40–50° C. to avoid gelling. The sutures are dipped in the coating solution for a period of time sufficient to provide a suitable coating, preferably at least 1 minute, more preferably at least 2 minutes, and most preferably from about 5 to 10 minutes. Longer periods of time, e.g., 5–10 minutes, allow the gut suture to swell and the gelatin to penetrate the interstices of the suture where it is later cross-linked.

The sutures can be immersed in a coiled configuration or straight configuration. After immersion for the specified duration of time the sutures are removed and placed in the fixative solution.

The fixative solution is an aqueous solution of a cross-linking agent. The preferred cross-linking agent is preferably a dialdehyde such as glutaraldehyde or glyoxal, which may be used alone or in conjunction with formaldehyde or other aldehydes. The cross-linking agent fixes the gelatin and renders it substantially insoluble in the tubing solution in which the suture will subsequently be stored.

The concentration of cross-linking agent preferably ranges from about 0.1% to about 5%, more preferably from about 0.3% to about 2%, and most preferably from about 0.5% to about 1%. The fixative solution is maintained at about room or ambient temperature. Treatment time in the fixative solution preferably ranges from about 1 minute to 30 minutes, more preferably about 5 minutes to about 20 minutes, and most preferably about 5 minutes to about 10 minutes.

Optionally, the sutures can be sequentially dipped in a first cross-linking agent followed by removal of the sutures from the first fixative solution and then dipping the sutures in a second cross-linking agent. Preferably, the first cross-linking agent is formaldehyde and the second cross-linking agent is glutaraldehyde.

After the sutures are removed from the fixative solution they are soaked in a buffer solution for a period of time preferably ranging from about 1 minute to about 5 minutes. The buffer solution maintains a pH of from about 7.2 to 7.6 and preferably about 7.4. Optionally, after a first buffer soaking the sutures can be soaked again in a second buffer solution.

After the sutures are soaked in buffer solution they are secured to a metal frame and dried for a sufficient period of time. Surprisingly, drying in air at room temperature does not produce satisfactory results. Rather, drying is preferably done by subjecting the sutures to a vacuum at a temperature of about 50° C. to about 90° C., and more preferably from about 70° C. to about 80° C. Alternatively, drying can be performed in a convection oven in flowing dry nitrogen at a temperature of from about 50° C. to about 90° C., and more preferably from about 70° C. to about 80° C. Drying time in a vacuum or nitrogen flow preferably ranges from about 1 to about 20 hours, more preferably about 4 to about 18 hours, and most preferably from about 8 to about 16 hours.

After the sutures are dried they are immersed in a tubing fluid for storage. Various compositions of tubing fluids are known in the art. A tubing fluid suitable for the use described herein includes water, isopropanol, and triethanolamine (TEA) in the following percentages: 12% water, 86.6% isopropanol, and 1.4% TEA.

Catgut sutures can be individually packaged and shipped in tubing fluid and stored for later use by a surgeon in an operation. When the catgut sutures are removed they retain the gelatin coating and exhibit superior handling characteristics and fray resistance as opposed to sutures which have not been treated in accordance with the method described above. Examples of suture coating are provided below. Comparative Examples A to D are experimental controls which are not performed in accordance with the method described above. The remainder of the Examples illustrate the method described herein. Suture handling characteristics were tested manually by loosely tying an overhand knot in the suture and running the knot down the length of the suture. Surface roughness was estimated by tactile observation. Fraying was observed visually.

EXAMPLE 1

A 4% aqueous solution of gelatin was prepared by adding 4.0 grams of gelatin powder into a 400 ml beaker and 96.0 cc of pyrogen free water and stirring at 60° C. until a homogenous solution was obtained. The gelatin solution was maintained warm at least at 50° C. degrees centigrade to avoid gelling. Chromic gut sutures of size 1 were coiled and dropped into the warm gelatin solution for about 1 minute. The dipped gut sutures were removed from the gelatin solution and introduced in 0.5% aqueous glutaraldehyde solution for 5 minutes. The glutaraldehyde treated sutures were then removed and dipped in a buffer of pH 7.4 for 1 minute. The sutures were finally removed from the buffer, uncoiled, and secured to a metal frame. The metal frame with coated gut sutures was heated in a vacuum oven at 80° C. at a vacuum of less than a torr for 16 hours. The resulting gut sutures were then introduced into a gut fluid containing 12.0 grams of water, 86.6 grams isopropanol and 1.4 grams triethanolamine. The coated chromic gut sutures did not fray even after 18 knot runs.

EXAMPLE 2

A 4% aqueous solution of gelatin was prepared by adding 4.0 grams of gelatin powder in a 400 ml beaker and 96.0 cc of pyrogen free water and stirring at 60° C. until a homogenous solution was obtained. To this, 0.5 grams of glycerol was added as a plasticizer. The gelatin-glycerol solution was maintained at least at 50° C. to avoid gelling. The chromic gut sutures size 1 were coiled and dropped into the warm gelatin solution for about 1 minute. The dipped gut sutures were removed from the gelatin solution and introduced into 0.5% glutaraldehyde solution for 5 minutes. The glutaraldehyde treated sutures were then removed and dipped into a buffer of pH 7.4 for 1 minute. The sutures were finally removed from the buffer, uncoiled, and secured to a metal frame. The metal frame with coated gut sutures was heated in a vacuum oven at 80° C. for at a vacuum of less than a torr for 16 hours. The resulting gut sutures were then introduced into a gut fluid containing 12.0 grams of water, 86.6 grams isopropanol and 1.4 grams triethanolamine. The coated gut sutures did not fray even after 18 knots.

EXAMPLE 3

A 4% aqueous solution of gelatin was prepared by adding 4.0 grams of gelatin powder into a 400 ml beaker and 96.0 cc of pyrogen free water and stirring at 60° C. until a homogenous solution was obtained. To this 4.0 grams of glycerol was added as a plasticizer. The gelatin glycerol solution was maintained at least at 50° C. to avoid gelling. The chromic gut sutures size 1 were coiled and dropped into the warm gelatin solution for about 5 minutes. The dipped gut sutures were then removed from the gelatin solution and introduced into 1.0% aqueous formaldehyde solution for 10 minutes. The formaldehyde treated sutures were then removed and dipped into a buffer at pH 7.4 for 1 minute. The sutures were finally removed, uncoiled, and secured to a metal frame. The metal frame with coated gut sutures were heated in a vacuum oven at 80° C. at a vacuum of less than a torr for 16 hours. The resulting coated chromic gut sutures were then introduced into gut tubing fluid containing 12.0 grams of water, 86.6 grams isopropanol and 1.4 grams triethanolamine. Upon testing, the coated sutures did not fray even after 18 knots.

EXAMPLE 4

An 8% aqueous solution of gelatin was prepared by adding 8.0 grams of gelatin powder into a 400 ml beaker and 92.0 cc of pyrogen free water and stirring at 60° C. until a homogenous solution was obtained. The chromic gut sutures size 1 were coiled and dropped into the warm (50° C.) gelatin solution for about 6 minutes. The dipped gut sutures were removed from the gelatin solution and introduced into 0.5% aqueous glutaraldehyde solution for 20 minutes. The glutaraldehyde treated sutures were then removed and dipped into a buffer of pH 7.4 for 2 minutes. The buffer treated sutures were again dipped in fresh buffer of pH 7.4 for another 1 minute. The sutures were finally removed from the second buffer bath, uncoiled, and secured to a metal frame. The metal frame with coated gut sutures were heated in a vacuum oven at 50° C. at a vacuum of less than a torr for 4 hours. The resulting gut sutures were then introduced into a gut fluid containing 12.0 grams of water, 86.6 grams isopropanol and 1.4 grams triethanolamine. Table top knot run down results showed that more than 15 knots could be put in the suture. Fraying occurred only after the 15th knot run down.

EXAMPLE 5

An 8% aqueous solution of gelatin was prepared by adding 8.0 grams of gelatin powder into a 400 ml beaker and 92.0 cc of pyrogen free water and stirring at 60° C. until a homogenous solution is obtained. The chromic gut sutures size 1 were coiled and dropped into warm (50° C.) gelatin solution for about 6 minutes. The dipped gut sutures were removed from the gelatin solution and introduced into 0.5% aqueous glutaraldehyde solution for 20 minutes. The glutaraldehyde treated sutures were then removed and dipped into a buffer of pH 7.4 for 2 minutes. The buffer treated sutures were again dipped in fresh buffer of pH 7.4 for another 1 minute. The sutures were finally removed from the second buffer bath, uncoiled, and secured to a metal frame. The metal frame with coated gut sutures were heated in a vacuum oven at 50° C. at a vacuum of less than a torr for 16 hours. The resulting coated chromic gut sutures were then introduced into gut tubing fluid containing 12.0 grams of water, 86.6 grams isopropanol and 1.4 grams triethanolamine. Table top knot run down results showed that more than 15 knots could be put in. Fraying did not occur even after 15th knot run down.

EXAMPLE 6

An 8% aqueous solution of gelatin was prepared by adding 8.0 grams of gelatin powder into a 400 ml beaker and 92.0 cc of pyrogen free water and stirring at 60° C. until a homogenous solution was obtained. Chrome Gut sutures size 1 were coiled and dropped into the warm (50° C.) gelatin solution for about 6 minutes. The dipped gut sutures were removed from the gelatin solution and introduced into 0.5% aqueous glutaraldehyde solution for 20 minutes. The glutaraldehyde treated sutures were then removed and dipped into a buffer of pH 7.4 for 2 minutes. The buffer treated sutures were again dipped in fresh buffer of pH 7.4 for another 1 minute. The sutures are finally removed from the second buffer bath, uncoiled, and secured to a metal frame. The metallic frame with coated gut sutures were heated in a convection oven at 80° C. for 4 hours in dry nitrogen with a flow rate of 5 cubic feet per minute.

The resulting coated chromic gut sutures were then introduced into gut tubing fluid containing 12.0 grams of water, 86.6 grams isopropanol and 1.4 gram triethanolamine.

Table top knot run down results showed that more than 15 knots could be put in. No fraying was observed until after the 15th knot run down.

EXAMPLE 7

An 6% aqueous solution of gelatin was prepared by adding 6 grams of gelatin in to a 400 ml beaker and 92 cc. of pryrogen free water and stirring at 60° C. until a homogenous solution was obtained. Chromic gut sutures, size 1 were dropped into a 46° C. gelatin solution for about 6 minutes. The gut sutures were removed from the gelatin solution and introduced into 0.5% aqueous glutaraldehyde solution for 1 minute. The glutaraldehyde treated sutures were then removed and dropped in to a buffer of pH 7.4 for 2 minutes. The buffer treated sutures were again dipped in fresh buffer of pH 7.4 for another 1 minute. The sutures were finally removed from the second buffer bath, uncoiled, and secured to a metallic frame. The metallic frame with coated sutures were heated in a convection oven at 60° C. for 1 hour in a dry nitrogen flow with a rate of 5 cubic feet per minute.

EXAMPLE 8

An 8% aqueous solution of gelatin was prepared by adding 8 grams of gelatin in to a 400 ml beaker and 92 cc. of pyrogen free water and stirring at 60° C. until a homogenous solution was obtained. Plain, size 1 gut sutures were dropped into 45° C. gelatin solution for about 6 minutes. The gut sutures were removed from the gelatin solution and introduced into 0.5% aqueous glutaraldehyde solution for 20 minutes. The glutaraldehyde treated sutures were then removed and dropped in to a buffer of pH 7.4 for 2 minutes. The buffer treated sutures were again dipped in fresh buffer of pH 7.4 for another 1 minute. The sutures were finally removed from the second buffer bath, uncoiled, and secured to a metallic frame. The metallic frame with coated sutures were heated in a convection oven at 60° C. for 4 hours in a dry nitrogen flow with a rate of 5 cubic feet per minute.

The resulting coated plain gut sutures were then introduced into a tubing fluid containing 12 grams of water, 86.6 grams of isopropanol and 1.4 grams of triethanolamine. Table top knot run down results showed that more than 15 knots could be put in. No fraying was observed until after 15 knot run. These results show the unexpected superior performance of gut sutures coated with gelatin in accordance with the method described herein even after being stored in tubing solution. The Comparative Examples presented below show that sutures which are untreated (Comparative Example A), coated but not fixed (Comparative Example B), dipped in fixative but not coated (Comparative Example C), and, surprisingly, coated and fixed but not heated (Comparative Example D), exhibited inferior handling properties.

Example 1 shows the improved results obtained by the present method. Examples 2 and 3 also showed improved results with a glycerol plasticizer. Example 3 also shows that formaldehyde can be used as a fixative. Examples 4 and 5 illustrate the use of double buffering and different heating times. Example 6 shows the use of a convection oven for heating at standard pressure also achieves good results.

Referring now to FIG. 1, a suture containing package 10 includes an envelope 11 sealed around the edges 12 with gelatin coated gut suture 14 immersed in tubing fluid 13. The envelope is fabricated from a material impervious to fluid, such as plastic or metal foil. The suture and tubing fluid can be sterilized by heat treatment to a suitable sterilization temperature and/or by incorporating suitable germicides in the tubing fluid, such as e.g., phenyl mercuric benzoate. The suture 14 and tubing fluid 13 are as described above. In another embodiment 20 the container 21 is a tubular ampule and sealed with a stopper 12. The container can be fabricated from glass or plastic. The gelatin coated gut suture 24 and tubing fluid 13 contained in the ampule 21 are as described above.

Comparative Example A

An untreated size chromic 1 gut suture was manually tested for handling characteristics. The suture was rough and broke after 6 knot run downs.

Comparative Example B

A 4% aqueous solution of gelatin was prepared by adding 4.0 grams of gelatin powder into a 400 ml beaker and 96.0 cc of pyrogen free water and stirring at 60° C. until a homogenous solution was obtained. The gelatin solution was maintained at least at 50° C. to avoid gelling. Chromic gut sutures size 1 were coiled into circles and dropped into the warm gelatin solution for about 2 minutes. The dip coated gut sutures were removed from the gelatin solution, un-coiled, and secured to a metal frame and dried at room temperature for 16 hours without soaking in fixative solution. The resulting gut sutures were then introduced into gut tubing fluid containing 12.0 grams of water, 86.6 grams isopropanol and 1.4 grams triethanolamine. The sutures were tested for fray on table top. The sutures frayed after 3 knot runs.

Comparative Example C

Chromic, size 1 gut sutures were coiled and dipped into 0.5% aqueous glutaraldehyde solution for 20 minutes without presoaking in gelatin solution. The treated sutures were then removed and dipped into a buffer of pH 7.4 for 1 minute. The sutures were finally removed from the buffer, uncoiled, and secured to a metal frame. The metal frame with coated gut sutures were heated in a vacuum oven at 80° C. at a vacuum of less than a milli torr for 16 hours.

The resulting gut sutures were then introduced into gut tubing fluid containing 12.0 grams of water, 86.6 grams isopropanol and 1.4 grams triethanolamine. The sutures frayed after 2 knot run downs. The run down was rough.

Comparative Example D

An 8% aqueous solution of gelatin was prepared by adding 8.0 grams of gelatin powder into a 400 ml beaker and 92.0 cc of pyrogen free water and stirring at 60° C. until a homogenous solution was obtained. Chromic gut sutures size 1 were coiled and dropped into the warm (50° C.) gelatin solution for about 6 minutes. The dipped gut sutures were removed from the gelatin solution and introduced into 0.5% aqueous glutaraldehyde solution for 20 minutes. The glutaraldehyde treated sutures were then removed and dipped into a buffer of pH 7.4 for 2 minutes. The buffer treated sutures were then again dipped in fresh buffer of pH 7.4 for another 1 minute. The sutures were finally removed from the second buffer bath, uncoiled, and secured to a metal frame.

The metal frame with coated gut sutures were kept at room temperature 16 hours, but were not heated in vacuo. The resulting gut sutures are then introduced into a gut tubing fluid containing 12.0 grams of water, 86.6 grams isopropanol and 1.4 grams triethanolamine.

Table top knot run down results showed that coated, but not heat treated gut suture was rough, frayed immediately, and broke after 8 runs.

It will be understood that various modifications may be made to the embodiments disclosed herein. Therefore the above description should not be construed as limiting but merely as exemplifications of preferred embodiments. Those skilled in the art will envision other modifications within the scope and spirit of the claims appended hereto.

What is claimed is:

1. A method for making a coated suture, comprising:
   a) contacting a gut suture with an aqueous solution of gelatin to coat the gut suture with gelatin;
   b) contacting the coated gut suture with at least one fixative to cross-link the gelatin agent;
   c) contacting the coated gut suture with a buffer; and
   d) heating the coated gut suture to a temperature of at least about 50° C. to dry the coated suture.

2. A method of claim 1 wherein the gut suture is selected from the group consisting of chromic and plain gut sutures.

3. The method of claim 1 further including the step: of storing the suture in a tubing solution.

4. The method of claim 3 wherein the tubing solution comprises water and at least one fluid selected from the group consisting of ethanol, isopropanol, triethanolamine, and mixtures thereof.

5. The method of claim 1 wherein said contacting step is accomplished by dipping the gut suture into a gelatin solution for at least about 1 minute.

6. The method of claim 1 wherein said gelating solution ranges in concentration from about 1% to about 10%.

7. The method of claim 1 wherein the gelatin solution also contains a plasticizer.

8. The method of claim 1 wherein the fixative comprises an aqueous solution of a cross linking agent selected from the group consisting of glutaraldehyde, formaldehyde and glyoxal.

9. The method of claim 8 wherein the concentration of cross linking agent ranges from about 0.3% to about 2%.

10. The method of claim 1 wherein said step of contacting the coated gut suture with a fixative comprises immersing the gut suture in an aqueous solution of a cross linking agent for a period of time ranging from about 1 minute to about 30 minutes.

11. The method of claim 1 wherein the buffer maintains a pH of from about 7.2 to about 7.6.

12. The method of claim 1 wherein the step of heating the coated gut suture comprises heating the coated gut suture in a vacuum for a period of time ranging from about 1 to about 20 hours.

13. A gut suture treated in accordance with the method of claim 1 and stored in a tubing solution.

14. The gut suture of claim 13 wherein said tubing solution comprises water and at least one fluid selected from the group consisting of ethanol, isopropanol, and triethanolamine.

15. A packaged suture comprising:
   a) a tubing solution;
   b) a gut suture that includes a cross linked gelatin coating which is substantially insoluble in the tubing solution; and
   c) a liquid-tight package containing the tubing solution and the gut suture.

16. A packaged suture as in claim 15 wherein the tubing solution comprises one or more fluids selected from the group consisting of water, ethanol, isopropanol and triethanolamine.

17. A method for making a coated gut suture, comprising:
   a) contacting a gut suture with an aqueous solution of gelatin containing a glycerol to coat the gut suture with gelatin solution;
   b) contacting the coated gut suture with at least one fixative agent;
   c) contacting the coated gut suture with at least one buffer;
   d) heating the coated gut suture to a temperature of at least about 50° C. to dry the coated suture.

18. The method of claim 17, wherein the weight ratio of glycerol to gelatin ranges from up to about 1:1.

19. The method of claim 17, wherein the step of heating the coated gut suture comprises heating the coated gut suture in a stream of flowing dry nitrogen for a period of time ranging from about 1 hour to about 20 hours.

20. A gut suture having a cross linked gelatin coating which is insoluble in a tubing solution containing water and alcohol including a plasticizer selected from the group consisting of glycerol and triethylcitrate.

* * * * *